US008409848B2

(12) United States Patent
Zeng et al.

(10) Patent No.: US 8,409,848 B2
(45) Date of Patent: Apr. 2, 2013

(54) SYSTEM AND METHOD FOR RAPID THERMAL CYCLING

(76) Inventors: Shulin Zeng, Gaithersburg, MD (US); Kenton C. Hasson, Gaithersburg, MD (US); Gregory A. Dale, Gaithersburg, MD (US); John Keady, Fairfax Station, VA (US)

( * ) Notice: Subject to any disclaimer, the term of this patent is extended or adjusted under 35 U.S.C. 154(b) by 64 days.

(21) Appl. No.: 11/770,911

(22) Filed: Jun. 29, 2007

(65) Prior Publication Data

US 2008/0176289 A1 Jul. 24, 2008

Related U.S. Application Data

(60) Provisional application No. 60/806,440, filed on Jun. 30, 2006.

(51) Int. Cl.
*C12M 1/34* (2006.01)
*C12Q 1/68* (2006.01)
*C12P 19/34* (2006.01)
(52) U.S. Cl. .............. 435/287.2; 435/6.12; 435/91.2
(58) Field of Classification Search .................. None
See application file for complete search history.

(56) References Cited

U.S. PATENT DOCUMENTS

| | | | |
|---|---|---|---|
| 4,676,274 A | 6/1987 | Brown | |
| 6,210,882 B1 | 4/2001 | Landers et al. | |
| 6,413,766 B2 | 7/2002 | Landers et al. | |
| 6,605,454 B2 | 8/2003 | Barenburg et al. | |
| 6,960,437 B2 | 11/2005 | Enzelberger et al. | |
| 2002/0001848 A1 | 1/2002 | Bedingham et al. | |
| 2002/0197603 A1* | 12/2002 | Chow et al. ............... 435/6 |
| 2004/0115838 A1 | 6/2004 | Quake et al. | |
| 2004/0131345 A1* | 7/2004 | Kylberg et al. ......... 392/465 |
| 2004/0131504 A1 | 7/2004 | Landers et al. | |
| 2005/0012982 A1 | 1/2005 | Behfar | |
| 2005/0042639 A1 | 2/2005 | Knapp et al. | |
| 2005/0191757 A1 | 9/2005 | Melker et al. | |

FOREIGN PATENT DOCUMENTS

| | | |
|---|---|---|
| EP | 1628137 A1 | 2/2006 |
| WO | 9641864 | 12/1996 |
| WO | 02/41998 A1 | 5/2002 |
| WO | 2004033099 A2 | 4/2004 |
| WO | 2005075683 A1 | 8/2005 |
| WO | 2006069305 A2 | 6/2006 |

OTHER PUBLICATIONS

Lagally et al., "Single-molecule DNA amplification and analysis in an integrated microfluidic device," Anal. Chem. 73:565-570 (2001).
Kopp et al., "Chemical amplification: continuous-flow PCR on a chip," Science, 280:1046-1048, (1998).
Park et al. "Cylindrical compact thermal-cycling device for continuous-flow polymerase chain reaction," Anal. Chem., 75:6029-6033 (2003).

* cited by examiner

*Primary Examiner* — Kenneth R. Horlick
*Assistant Examiner* — David Thomas
(74) *Attorney, Agent, or Firm* — Rothwell, Figg, Ernst & Manbeck, P.C.

(57) ABSTRACT

At least one exemplary embodiment is directed to an apparatus that includes a microfluidic channel and at least one energy absorbing element, where the energy absorbing element is configured to absorb at least a portion of an incident electromagnetic radiation. The absorption of the radiation by the energy absorbing element varies the temperature of a sample in the microfluidic channel.

36 Claims, 9 Drawing Sheets

SYSTEM AND METHOD FOR RAPID THERMAL CYCLING

This application claims the benefit of U.S. Provisional Patent Application No. 60/806,440, filed on Jun. 30, 2006, which is incorporated herein by this reference.

BACKGROUND

1. Field of the Invention

The present invention relates to microfluidic thermal control, and in particular, though not exclusively, to thermal control of microfluidic DNA analysis systems using electrical and/or magnetic (hereafter electromagnetic) radiation as an energy source.

2. Related Art

The detection of nucleic acids is central to medicine, forensic science, industrial processing, crop and animal breeding, and many other fields. The ability to detect disease conditions (e.g., cancer), infectious organisms (e.g., HIV), genetic lineage, genetic markers, and the like, is ubiquitous technology for disease diagnosis and prognosis, marker assisted selection, correct identification of crime scene features, the ability to propagate industrial organisms and many other techniques. Determination of the integrity of a nucleic acid of interest can be relevant to the pathology of an infection or cancer. One of the most powerful and basic technologies to detect small quantities of nucleic acids is to replicate some or all of a nucleic acid sequence many times, and then analyze the amplification products. Polymerase chain reaction (PCR) is a well-known technique for amplifying DNA.

With PCR, one can quickly produce millions of copies of DNA starting from a single template DNA molecule. PCR includes a three phase temperature cycle of denaturation of the DNA into single strands, annealing of primers to the denatured strands, and extension of the primers by a thermostable DNA polymerase enzyme. This cycle is repeated a number of times so that at the end of the process there are enough copies to be detected and analyzed. For general details concerning PCR, see Sambrook and Russell, *Molecular Cloning—A Laboratory Manual* (3rd Ed.), Vols. 1-3, Cold Spring Harbor Laboratory, Cold Spring Harbor, N.Y. (2000); *Current Protocols in Molecular Biology*, F. M. Ausubel et al., eds., Current Protocols, a joint venture between Greene Publishing Associates, Inc. and John Wiley & Sons, Inc., (supplemented through 2005) and *PCR Protocols A Guide to Methods and Applications*, M. A. Innis et al., eds., Academic Press Inc. San Diego, Calif. (1990).

Recently, a number of high throughput approaches to performing PCR and other amplification reactions have been developed. In many of these new approaches amplification reactions take place in a microfluidic device. Thermal cycling of the sample for amplification is usually accomplished in one of two methods. In the first method, the sample solution is loaded into the device and the temperature is cycled in time, much like a conventional PCR instrument. In the second method, the sample solution is pumped continuously through spatially varying temperature zones. See, for example, Lagally et al. (*Anal Chem* 73:565-570 (2001)), Kopp et al. (*Science* 280:1046-1048 (1998)), Park et al. (*Anal Chem* 75:6029-6033 (2003)), Hahn et al. (WO 2005/075683), Enzelberger et al. (U.S. Pat. No. 6,960,437) and Knapp et al. (U.S. Patent Application Publication No. 2005/0042639).

Microfluidic systems are systems that have at least one channel through which a fluid may flow, which channel has at least one internal cross-sectional dimension, (e.g., depth, width, length, diameter) that is less than about 1000 micrometers.

There is current market interest in further developing microfluidic genomic sample analysis systems for detecting DNA sequences. The development of these microfluidic systems often entail the various combinations of channel configurations, inlets, outlets, buffer insertion methods, boluses of genomic sample insertion methods, temperature cycling and control methods, and optical analysis methods.

Temperature cycling (thermocyling) and control of samples in a microfluidic system, is an important feature, and varies with particular genomic samples and assays. For example, assays involving denaturation of proteins or thermal cycling reactions during primer extension and nucleic acid amplification reactions require temperature regulation. For example, a typical DNA amplification by polymerase chain reaction (PCR) cycle will cycle the temperature of the genomic sample from about 95° C. for denaturing, to about 55° C. for annealing, then to about 72° C. for extension forming a single PCR cycle. A number of different options are available for achieving such regulation that vary in degree of sophistication.

One specific approach for regulating temperature within the devices is to employ external temperature control sources. Examples of such sources include heating blocks and water baths. Another option is to utilize a heating element such as a resistive heater that can be adjusted to a particular temperature. Such heaters are typically utilized when one seeks to simply maintain a particular temperature. Another suitable temperature controller includes Peltier controllers (e.g., INB Products thermoelectric module model INB-2-(11-4)1.5). This controller is a two stage device capable of heating to 94° C. Such a controller can be utilized to achieve effective thermal cycling or to maintain isothermal incubations at any particular temperature (see discussion in U.S. Application Pub. No. 2004/0115838).

In some devices and applications, heating of a sample directly from a remote heat source has been described, for example, a heating system discussed by Landers (WO 2004/033099 A2), where the heating of a sample is accomplished through the use of energy from a remote heat source, for example infrared (IR). The IR wavelengths are directed to a vessel containing the sample, and because the vessel is made of clear or translucent material, the IR waves act directly on the sample to cause heating of the sample (Landers, pg. 13, ll. 15-24), where heating of the sample is primarily caused by direct action of IR wavelengths on the sample itself. However, for such a system, the absorptive nature of each sample has to be matched to the optical wavelengths of the remote heat source, resulting in a reduced accuracy of temperature stability of a sample depending upon its absorptive characteristics. Decreased temperature stability can result in longer thermal cycling speeds, since it can be difficult to determine the stable temperature at which to plateau, where the thermal cycling speed refers to the time between stabilization from one temperature to another in a heating cycle.

For example, in the PCR process, the thermal cycling speed refers to the time to shift from 95° C. to 55° C. to 72° C. FIG. 1 illustrates a typical variation of temperature zones (A (94° C.), B (52° C.), and C (72° C.)) involved in a conventional PCR process. The faster the thermal cycling speeds and the more accurate the temperature stabilization, the more efficient PCR processes can be performed. Thus, in conventional systems, temperature accuracy and thermal cycling speeds are issues to be resolved.

Additional systems described by Landers et al. (U.S. Pat. No. 6,210,882 and U.S. Pat. No. 6,413,766) are similar to the system described above. For example, they have sample heating occurring by directed sample heating by the IR waves.

In addition to IR remote heating several systems have discussed the use of microwaves to heat the samples directly. For example microwave mediated PCR has been demonstrated using macro volumes with 2.5 mL (Orrling et al., Chem. Comm., 2004, 790-791) and 100 µL reaction volumes (Fermer et al., European Journal of Pharmaceutical Sciences 18:129-132, 2003). In these cases, single-mode microwave cavities were used to deliver microwave power to the sample, and due to the relatively large volumes of liquid being heated, these systems require very high microwave intensities in order to heat the solutions in a reasonable amount of time.

U.S. Pat. No. 6,605,454 to Barenburg et al., discloses a microwave device having a monolithic microwave integrated circuit (MMIC) disposed therein for heating samples introduced into a micro fluidic device and for effecting lysis of cells in the samples by applying microwave radiation. For efficient heating, the patent specifically targets dipole resonance frequency of water in the range of 18 to 26 GHz. This method, thus, is particularly efficient for heating water which is a major component of biological and most chemical systems studied in microfluidic devices. However, the high frequencies required with this approach render the system costly to operate and manufacture.

WO/2006/069305 by Landers et al. discusses a microwave heating system that has a frequency lower than that of the dipole resonance of water. The system described delivers microwave radiation in the frequency range of about 600 MHz-10 GHz. Since these frequencies are lower than the resonance frequency of water, heating efficiency may be improved through matching the impedance of a filled reaction chamber to the transmission line impedance. The microwave heating is controlled by either directly monitoring the solution temperature or, alternatively, remotely monitoring the solution temperature. The system in general delivers microwave radiation to a sample in a micro-area on a microfluidic device, where in one example conductors are placed adjacent to the micro-area for which microwave radiation is desired, where the conductors are close enough to deliver microwave radiation to the sample within the desired micro-area. Thus, as in the other systems discussed above, the system describes direct heating of the sample.

SUMMARY OF THE INVENTION

The present invention provides systems and method for more rapid thermal cycling.

In one particular aspect, the invention provides an apparatus for use in carrying out a reaction by thermal cycling. In some embodiments, the apparatus includes: a microfluidic chip; a microfluidic channel formed in the microfluidic chip, the microfluidic channel having at least one wall; an electromagnetic energy source configured and arranged to output radiation such that the radiation illuminates at least a portion of the microfluidic channel; and an energy absorption element configured to absorb at least a portion of the radiation, and, thus, heat when illuminated by the radiation, wherein the absorption element is positioned such that when absorption element is heated by the radiation the absorption element transfers heat to a sample that is in the microfluidic channel.

In other embodiments, the apparatus includes: a microfluidic chip comprising a microfluidic channel for containing a reaction sample; an energy absorbing element that is applied to and/or forms part of the microfluidic channel; heating means to heat the reaction sample; cooling means to cool the reaction sample; sensor means to sense the temperature of the reaction sample; and control means coupled to the sensor means for controlling the heating means.

In another aspect of the invention, the invention provides a method for cycling the temperature of a solution. In one embodiment, the method includes: (a) obtaining a chip having a microfluidic channel for receiving a solution comprising real-time PCR reagents; (b) introducing a solution comprising real-time PCR reagents into the microfluidic channel; (c) heating the solution while the solution moves through the microfluidic channel, wherein the act of heating the solution comprises exposing the microfluidic channel to electromagnetic radiation; (d) after heating the solution, cooling the solution while the solution moves through the channel; and (e) repeating steps (c) and (d) a number of times, wherein an energy absorbing element configured to absorb the electromagnetic radiation is suspended within the solution and/or forms part of the chip.

Further exemplary embodiments are described below. It should be understood that the detailed description and specific examples, while indicating exemplary embodiments of the invention, are intended for purposes of illustration only and are not intended to limit the scope of the invention.

DETAILED DESCRIPTION OF EXEMPLARY EMBODIMENTS

The following description of at least one exemplary embodiment is merely illustrative in nature and is in no way intended to limit the invention, its application, or uses. Processes, techniques, apparatus, and materials as known by one of ordinary skill in the relevant art may not be discussed in detail but are intended to be part of the enabling description where appropriate, for example the fabrication of the microfluidic channels, and the positioning of temperature detection devices. In all of the examples illustrated and discussed herein any specific values, for example the dimensions, number of microfluidic channels, number of detectors, pressures, temperature values of temperature zones, and flow rates, should be interpreted to be illustrative only and non limiting. Thus, other examples of the exemplary embodiments could have different values.

SUMMARY OF EXEMPLARY EMBODIMENTS

The first exemplary embodiment is directed to a temperature control apparatus that uses electromagnetic energy to heat a real-time PCR reagent fluid in a single microfluidic channel, where at least some of the electromagnetic energy is absorbed by at least one absorption element, which element transfers heat to the reagent fluid by at least one of radiation, convection, and conduction.

The second exemplary embodiment is directed to a temperature control apparatus that uses electromagnetic energy to heat a first PCR reagent fluid in a first microfluidic channel and a second PCR reagent fluid in a second microfluidic channel, where, for each channel, at least some of the electromagnetic energy is absorbed by at least one absorption element, which element transfers heat to the reagent fluid in the channel by at least one of radiation, convection, and conduction. In the second exemplary embodiment, each of the plurality of channels can be individually temperature controlled.

The third exemplary embodiment is directed to a temperature control apparatus that controls temperature zones on a microfluidic chip (e.g., via similar methods as controlling individual microfluidic channel temperature as in the first or second exemplary embodiment), through which at least one microfluidic channel passes. In illustrations of the third exemplary embodiment (e.g., FIG. 7) a single microfluidic channel is shown passing through three temperature zones. However the present invention is not limited to a single microfluidic channel passing through three temperature zones and other exemplary embodiments can have multiple (e.g., two or more) microfluidic channels passing through multiple temperature zones for example where one of the zones is not controlled.

First Exemplary Embodiment

Figure 1:
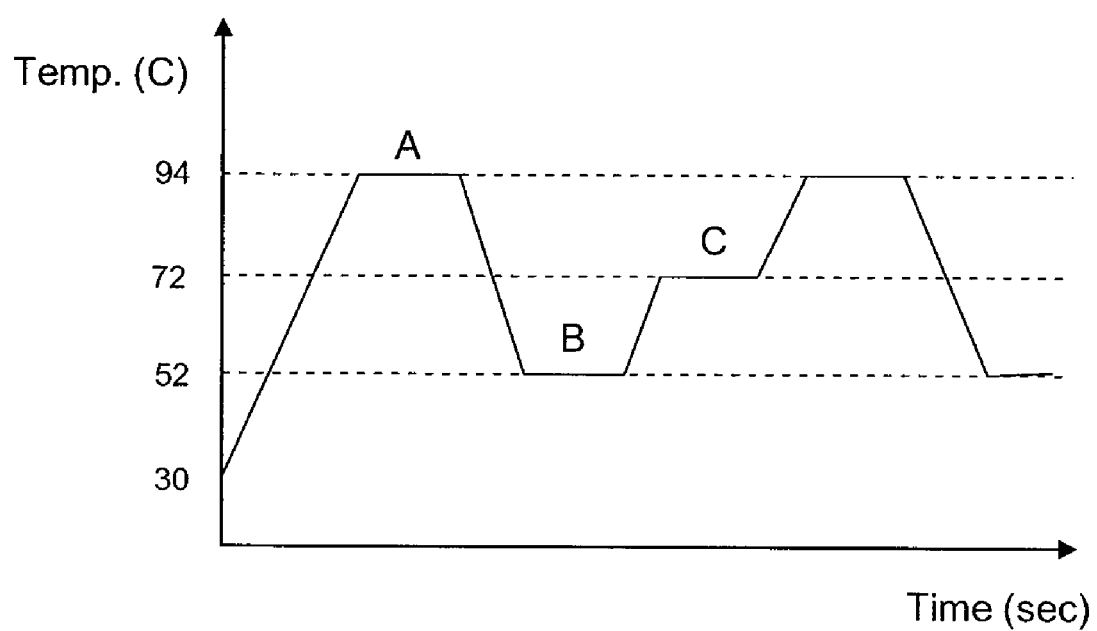
FIG. 1 illustrates a plot of the temperature change versus time for the various stages in a PCR process.
Figure 2:
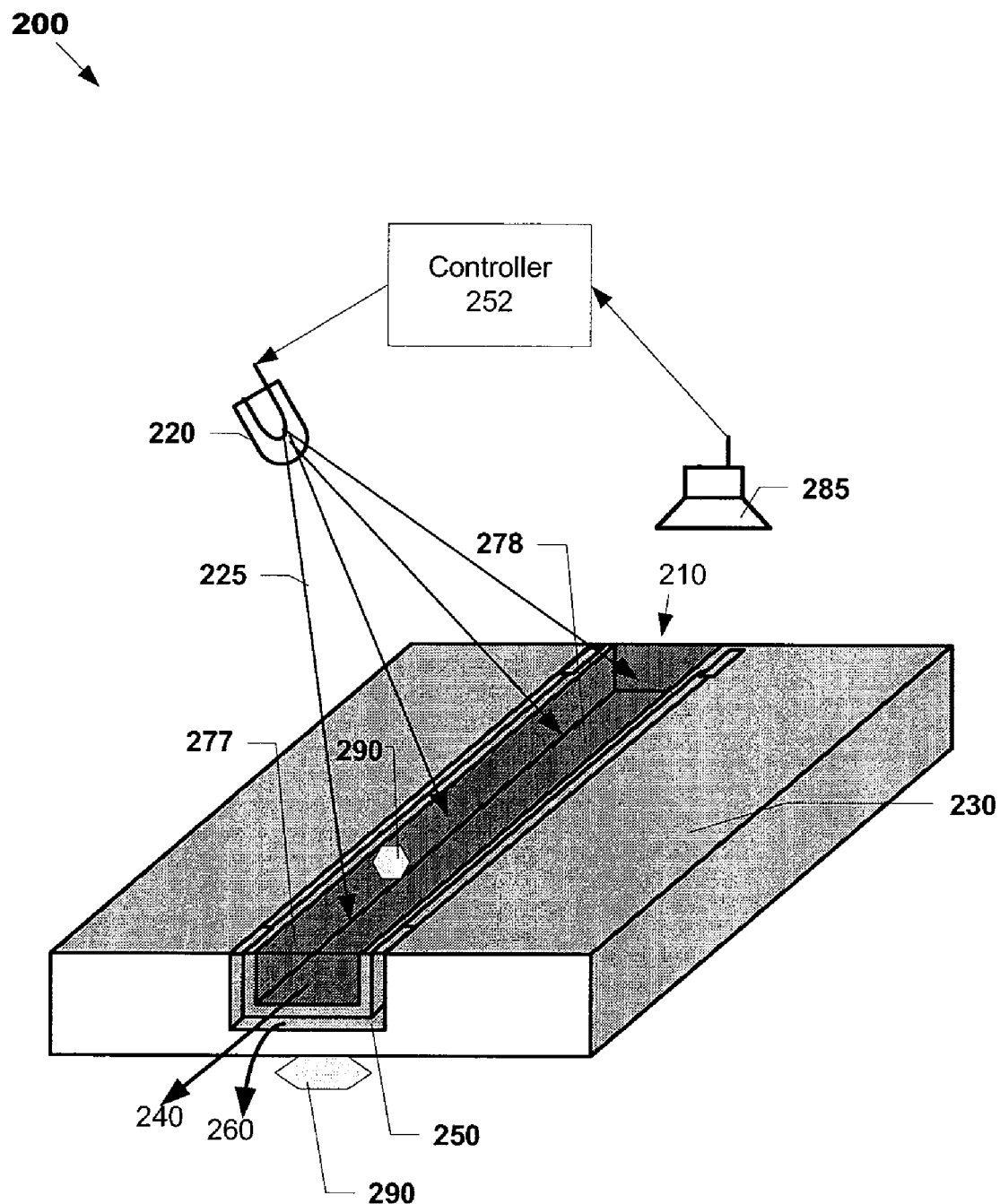
FIG. 2 illustrates an apparatus in accordance with at least one exemplary embodiment.

FIG. 2 illustrates an apparatus 200 according to some embodiments of the invention. As illustrated in FIG. 2, apparatus 200 may include: a microfluidic chip 230 and an electromagnetic energy source 220 (e.g., a source of infra-red (IR) energy, microwave energy, radio frequency (RF) energy, etc., or any combination thereof) for producing electromagnetic radiation 225. In some embodiments, source 220 is a laser that outputs radiation having a wavelength of between about 100 nanometers to 300 micrometers. In some embodiments, the laser outputs radiation having a wavelength of between about 200 nanometers to 20 microns.

Chip 230 may include at least one microfluidic channel 210 through which a PCR reagent fluid 240 may flow. Moving fluid 240 through the microfluidic channel 210 can be accomplished by a variety of methods, for example, via conventional methods of pressure-driven flow (e.g., using a pump to create a pressure differential) and the flow rates can vary, for example between 10 nanoliters per minute to 1 ml per minute.

In some embodiments, chip 230 may also include a heat-exchange channel 250 that may contain a heat-exchange fluid 260. In some embodiments, heat exchange channel 250 is not an integral part of chip 230, but is connected to chip 230. Fluid 260 may be in a liquid or gaseous state. In some embodiments, fluid 260 may flow through the channel. In other embodiments, fluid 260 may be stationary within channel, in which case heat exchange channel 250 may be in the form of a chamber.

In the exemplary embodiments, the chip 230 can include single or multiple microfluidic channels in either parallel or varying paths. The chip 230 can be made of plastics, glass, silica, quartz, silicon or any other material provided that at least one reagent fluid channel 210 (i.e., a micro channel configured to carry fluids) can be formed in or on the chip 230 and the contents of the channel can be imaged electromagnetically (e.g., optically in the infrared, UV, and/or visible bands). The at least one channel 210 can be formed by molding, etching (e.g., plasma etching), cutting, deposition or any other process or method as known by one of ordinary skill that can form a channel 210 in the chip 230. The chip can also be fabricated in any reasonable size in the range of 0.1 cm$^2$ to 100 cm$^2$. For example, in at least one exemplary embodiment the chip 230 is approximately 20 mm×20 mm, where the size can be driven by the design trade-offs of sample volume, PCR channel length, fluorescence signal measurement, and manufacture cost.

Radiation 225 produced by source 220 is used to heat the reagent fluid 240 flowing through channel 210. Accordingly, radiation 225 may be in the form of a beam that is similar in dimensions with channel 210 and is directed to the channel 210.

In the illustrated embodiment, an absorption element 290 may be added to the reagent channel 210 and/or added to the reagent fluid flowing through the channel and/or may be positioned near the channel. The absorption element 290 is configured and positioned such that when it is exposed to radiation 225 its temperature increases, which temperature increase causes a transfer of heat from the element 290 to adjacent elements by radiation, convection, and/or conduction. Accordingly, a reagent fluid 240 flowing through the channel 210 can be heated by, among other things, heat transfer between the absorptive element 290 and the fluid 240. Any samples (e.g., boluses, reagent) in the fluid 240 may also be heated or cooled via the heat transfer.

In some embodiments, absorption element 290 may include an element that is applied to one or more of the walls of channel 210 (e.g., side walls 277 and/or bottom wall 278). This element may include, for example, a black paint, a metal (e.g., iron, cobalt, aluminum, copper, platinum, etc), a carbon pad, or other absorption element. The metal may include a vapor deposited metal such as, for example, vapor deposited platinum.

Figure 3:
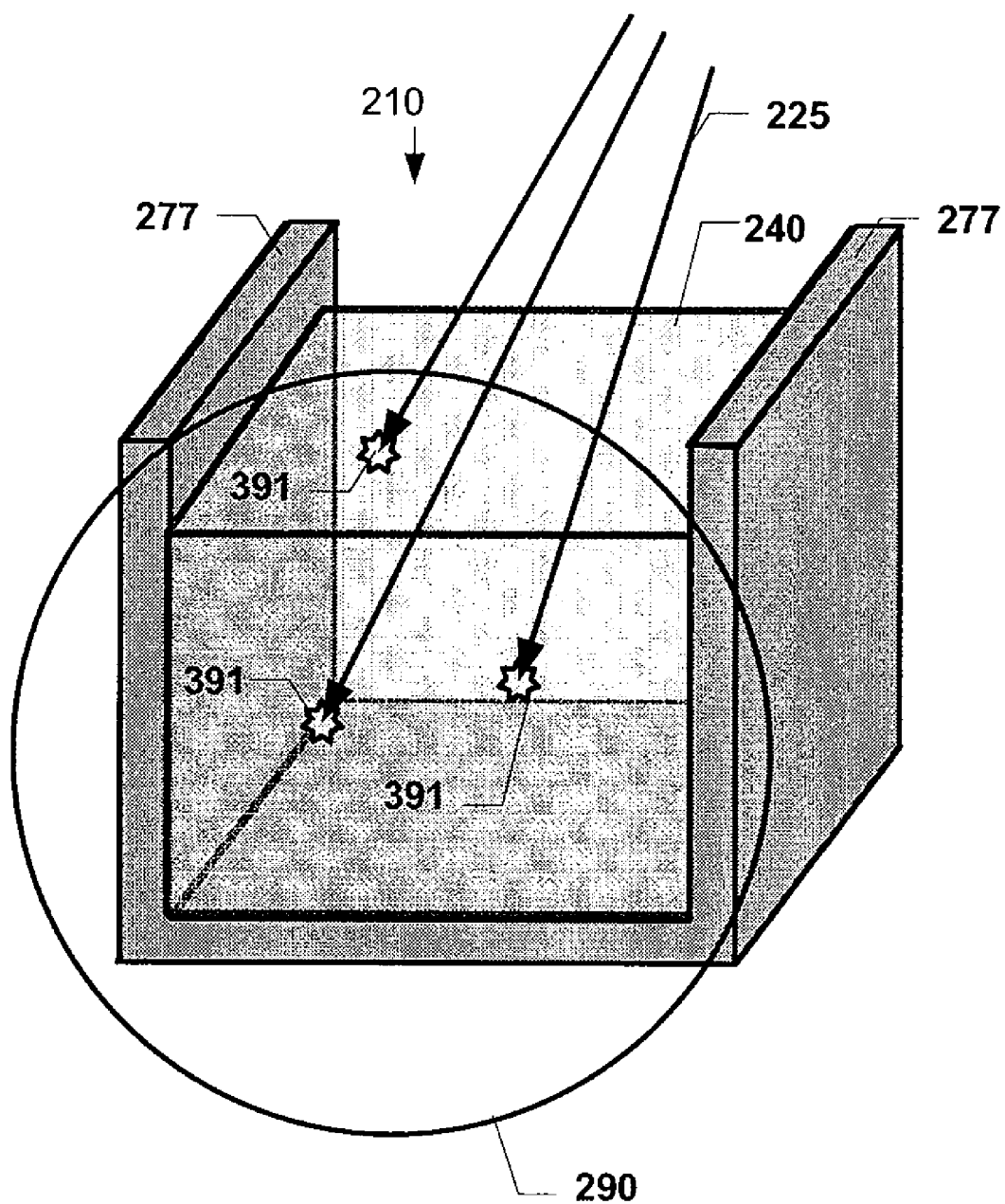
FIG. 3 illustrates an absorption element according to one exemplary embodiment.

In some embodiments, in addition to or instead of including an element applied to a wall of channel 210, absorption element 290 may include one or more discrete absorption particles 391 (see FIG. 3), which particles may be suspended in fluid 240 or attached to a wall of channel 210. Particles 391 may include metal particles, polymers and/or nanoparticles, such as, for example, super paramagnetic iron oxide nanoparticles, which may be used in conjunction with a microwave source 220, photothermal metallic nanoparticles (e.g., gold nanocrescent particles, nanoshells, nanorods, nanocages, nano-halfshells, etc), carbon nanotubes, etc. Also, in some embodiments element 290 may be positioned underneath channel 210 in addition to or instead of having an element 290 be positioned on a wall of channel 210 or within channel 210 or fluid 240.

It is preferred that element 290 absorb as much of the radiation 225 to which it is exposed as possible. That is, it is preferred, but not required, that element 290 absorb at least most of the radiation to which it is exposed. In terms of emissivity, it would be ideal, but not required, for element 290 to have an emissivity of 1. For most wavelengths of IR radiation, suitable elements for implementing element 290 may include elements having a black surface (e.g., a metal sheet having a flat, matt black surface).

In the case that source 220 produces an electromagnetic field 225 (e.g., an alternating field) in the RF wavelengths, element 290 may include electrically conducting materials (e.g., metallic particles) in which currents are induced when the particles are exposed to radiation 225. These induced currents cause element 290 to heat. Additionally or alternatively, element 290 may include a susceptor that heats in the presence of the varying RF field 225. The susceptor may include an ionic or polar compound and act as either a charge-carrying or an oscillating/vibrating component of the element 290. Susceptor compositions that cause heating in the presence of a varying RF electromagnetic field are well known in the art and described in, for example, U.S. Pat. No. 6,600,142.

In some embodiments, when source 220 is outputting radiation 225 for the purpose of heating fluid 240, an insulating fluid 260, such as air, may be injected into the heat-exchange channel 250 to prevent fluid 240 from losing heat. To further reduce heat loss in fluid 240, the fluid 260 that is injected into channel 250 may be heated. For example, it may be heated to a temperature that is higher than ambient temperature or to the temperature to which it is desired to heat fluid 240.

Figure 4:
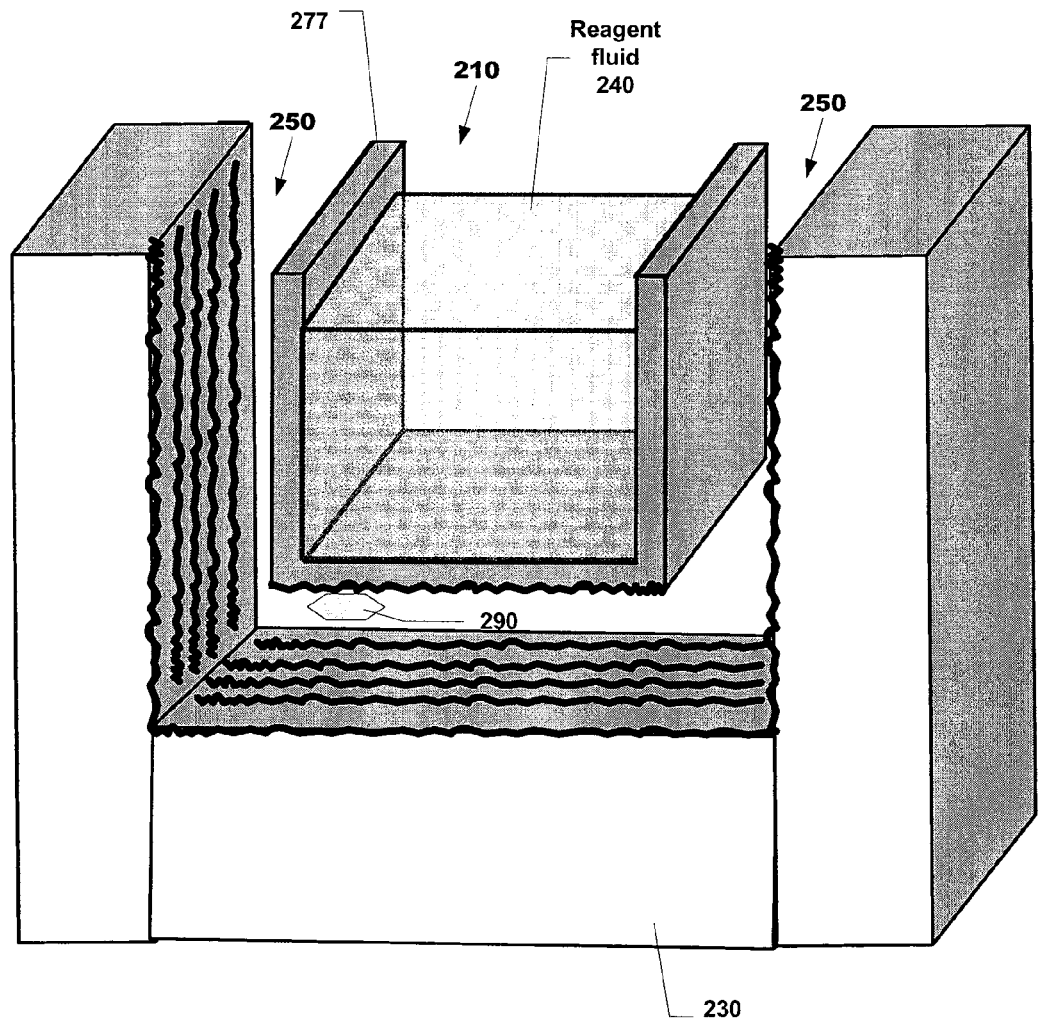
FIG. 4 illustrates a heat-exchange channel.

In some embodiments, it may be necessary to rapidly cool fluid 240 after its temperature has been raised. For example, in some embodiments, it may be necessary to raise the temperature of fluid 240 to about 95° C. and to hold the fluid 240 at that temperature for a predetermined amount of time and then, after the predetermined amount of time has expired, rapidly cool the fluid to about 55° C. Accordingly, when fluid 240 needs to be rapidly cooled, source 220 is "turned off" (i.e., configured to not produce any heat causing radiation) and the insulating fluid may be removed from channel 250 and then a cooling fluid may be introduced into channel 250. In one embodiment, a cooling fluid flows through or remains stationary within channel 250 when the temperature of fluid 240 needs to decrease. In some embodiments, to increase the effectiveness of the cooling fluid 260, one or more walls of the channel 250 may be a rough wall, rather than a smooth wall. This feature is illustrated in FIG. 4, which shows heat-exchange channel 250 having rough walls and also shows channel 210 being surrounded by channel 250 on three sides such that channel 250 is in the shape of a U with channel 210 running through channel 250. The rough walls of channel 250 may provide more surface area for heat transfer than smooth walls, and, in embodiments where the cooling fluid flows through channel 250, enhance heat transfer by introducing more turbulence during flow of the cooling fluid. A cooling fluid that has a temperature of about less than about 55 degrees centigrade should provide a driving force for heat transfer so that when the cooling fluid is introduced into channel 250 the temperature of the reagent fluid 240 may reduce rapidly.

Referring back to FIG. 2, in some embodiments, apparatus 200 may include a temperature sensor 285, which may be operable to sense the temperature of the fluid 240. The data from the sensor 285 can be used by a controller 252 to modify (e.g., via illumination reduction or increase) the output of source 220, thereby modifying the heating of element 290 and fluid 240. Controller 252 may also control heat-exchange channel 250. For example, if, based on data output from sensor 285, controller 252 determines that the temperature is too high, controller 252 may reduce the intensity of the output of source 220 and/or cause a cooling liquid to enter channel 250. In some embodiments, controller 252 is or includes a microprocessor based proportional-integral-derivative (PID) controller that receives as a control target a predefined temperature profile.

In some embodiments, sensor 285 is an IR sensor. Measuring temperature using an IR sensor may be very simple and reliable as long as the emissivity of the material being sensed is known. Accordingly, when using an IR sensor to measure temperature, it is advantageous to measure the temperature from a point of known emissivity. Black materials have an emissivity very close to 1.0, and it is very accurate to measure temperature from a black body using an IR thermometer. Thus, as in the case of heating using IR radiation, one may put black paint on a particular portion of chip 230 (e.g., on a wall of channel 210) and configure and arrange the IR sensor to detect the IR emissions from that particular portion of chip 230 (e.g., configure the focal plane of the IR sensor so that the focal plane is on the particular portion of chip 230). If the particular portion of the chip 230 is a portion of wall 277, for example, then the measured temperature may be very close to the temperature of the PCR reagent in channel 210 because of the small scale of channel 210. Thus, adding a black material to channel 210 may serve the dual purpose of facilitating heating of the sample in channel 210 and facilitating the measuring of the temperature of the sample.

Figure 5:
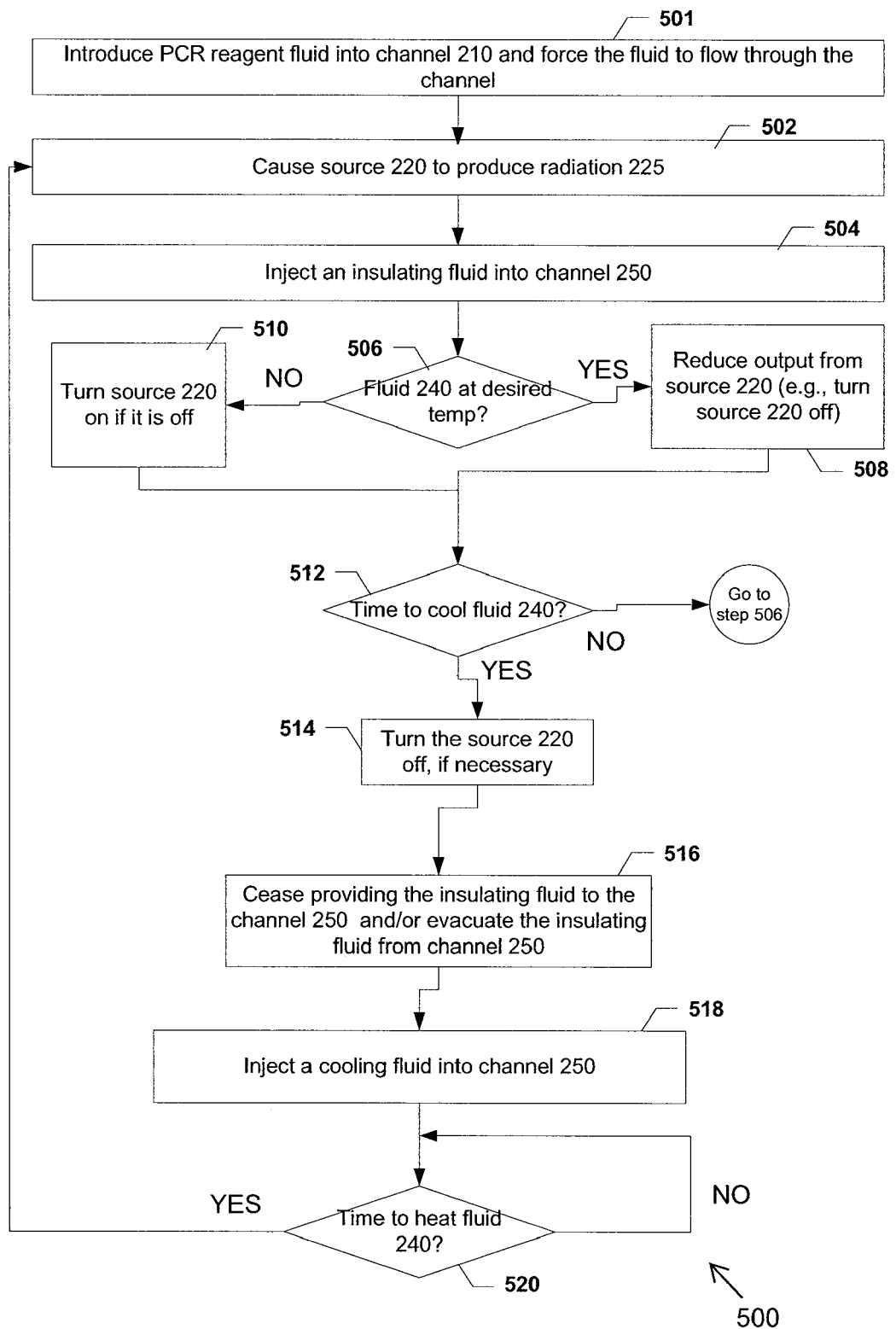
FIG. 5. is a flow chart illustrating a process according to an embodiment of the invention.

Referring now to FIG. 5, FIG. 5 is a flow chart illustrating a process 500 for heating and cooling PCR reagent 240. Process 500 may begin in step 501, where a sample containing PCR reagents 240 may be introduced into channel 210 and forced to flow through channel 210. In step 502, source 220 is activated (i.e., source 220 is configured to output radiation 225). Next, in step 504, which may occur at the same time as step 502 or before, an insulating fluid is injected into channel 250. In step 506, a determination is made as to whether fluid 240 has reached the desired temperature. If so, the process may proceed to step 508, otherwise the process may proceed to step 510. In step 508, controller 252 may reduce the output of source 220 (e.g., controller 252 may turn off source 220). In step 510, controller may increase the output of source 220. In step 512, a determination is made as to whether it is time to cool fluid 240. If it is time, process 500 may proceed to step 514, otherwise process 500 may proceed back to step 506. In step 514, source 220 is turned off. Next, in step 516, which may occur at the same time as step 508 or before, the insulating fluid is evacuated from channel 250. In step 518, a cooling fluid is injected into channel 250. In step 520, a determination is made as to whether it is time to cool fluid 240. If it is time, process 500 may proceed back to step 502.

Second Exemplary Embodiment

Figure 6:
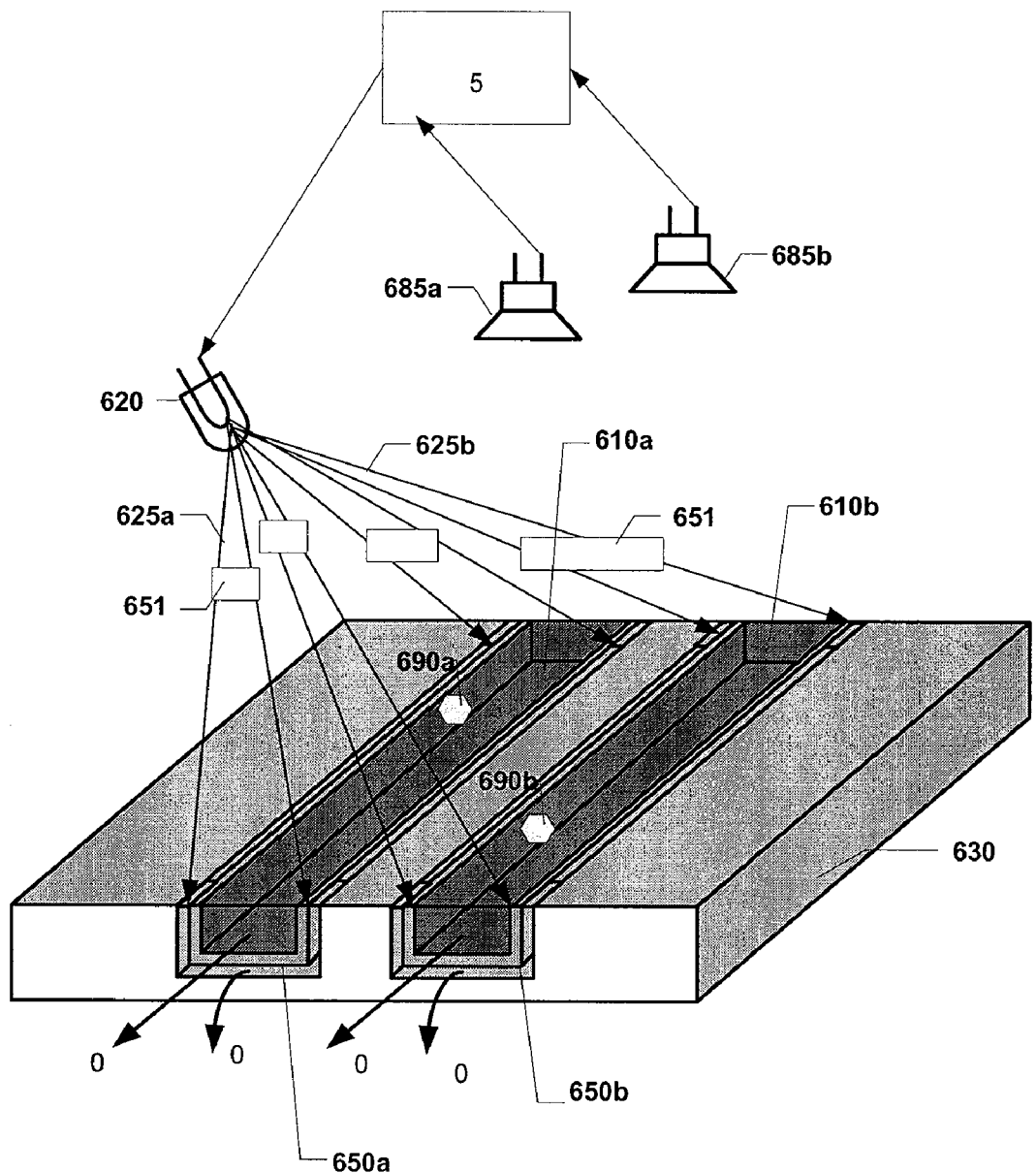
FIG. 6. illustrates an apparatus in accordance with at least one exemplary embodiment.

Referring now to FIG. 6, FIG. 6 illustrates an apparatus 600 in accordance with the second exemplary embodiment. An energy source 620 produces radiation 625a and 625b that illuminates a microfluidic chip 630 on two respective illumination portions of the microfluidic chip 630. The microfluidic chip 630 can include at least two microfluidic channels 610a and 610b, each associated with one of the two illumination portions. The microfluidic chip 630 can also optionally include heat-exchange channels 650a and 650b. In some embodiments, flows 660a and 660b may flow through channels 650a and 650b, respectively. At least a portion of the energy in the incident illumination 625a is absorbed by at least one absorption element 690a (e.g., which, as described above with reference to the first exemplary embodiment, can be a coating that covers at least a portion of a wall of channel 610a) operatively connected to the first microfluidic channel 610a. Similarly at least a portion of the energy in the incident illumination 625b is absorbed by at least one absorption element 690b operatively connected to the second microfluidic channel 610b.

The illuminations 625a and 625b can be varied in energy to vary the heating and/or cooling of the respective absorptive elements 690a and 690b, which can result in different stabilized temperatures of the respective microfluidic channels 610a and 610b. The variation in energy can be accomplished via an intervening filter or reflector 651, or can be accomplished via one or more energy sources 620 that can be configured to spatially vary the illumination intensities. For example, although FIG. 6 shows only a single source 620, more than one energy source 620 can be used. For example, one source associated with microfluidic channel 610a and the other with microfluidic channel 610b. Each of the two energy sources can be configured to emit different levels of illumination energy and/or intensity 625a and 625b at any given point in time. The different illuminations may result in different heat transfer to the two respective microfluidic channels 610a and 610b.

The temperature of each fluid 640a and 640b (and/or samples) flowing or stationary in either microfluidic channel 610a and 610b can be measured remotely via sensors 685a,b, respectively, and the data output from sensors 685a,b may be used by a controller 652 to either increase or decrease the illumination energies 625a and 625b. The change in illumination energy can control the heat transfer between the absorbing elements and hence can control the temperature of the fluids 640a and 640b.

As mentioned the fluids 640a and 640b flowing through their respective microfluidic channels 610a and 610b, can be heated or cooled by heat transfer between the absorptive element 690 and the fluids 640a and 640b. Any samples (e.g., boluses, reagent) in the fluids 640a and 640b can also be heated or cooled via the heat transfer. Optionally or additionally heat-exchange fluid 660a and 660b in (e.g., stationary or flowing) the respective heat-exchange channels can alter the amount of heat transfer between the absorptive elements and the fluid flows 640a and 640b and/or the samples (not shown, but for example can be an individual droplet traveling in the fluid 640a and/or 640b through the microfluidic channels 610a and/or 610b). Additionally the heat-exchange fluid 660a and 660b, where fluid refers to either a gas or liquid, can have a low thermal conductivity, thus isolating the thermal heating/cooling to the vicinity of the respective microfluidic channels.

Third Exemplary Embodiment

Figure 7:
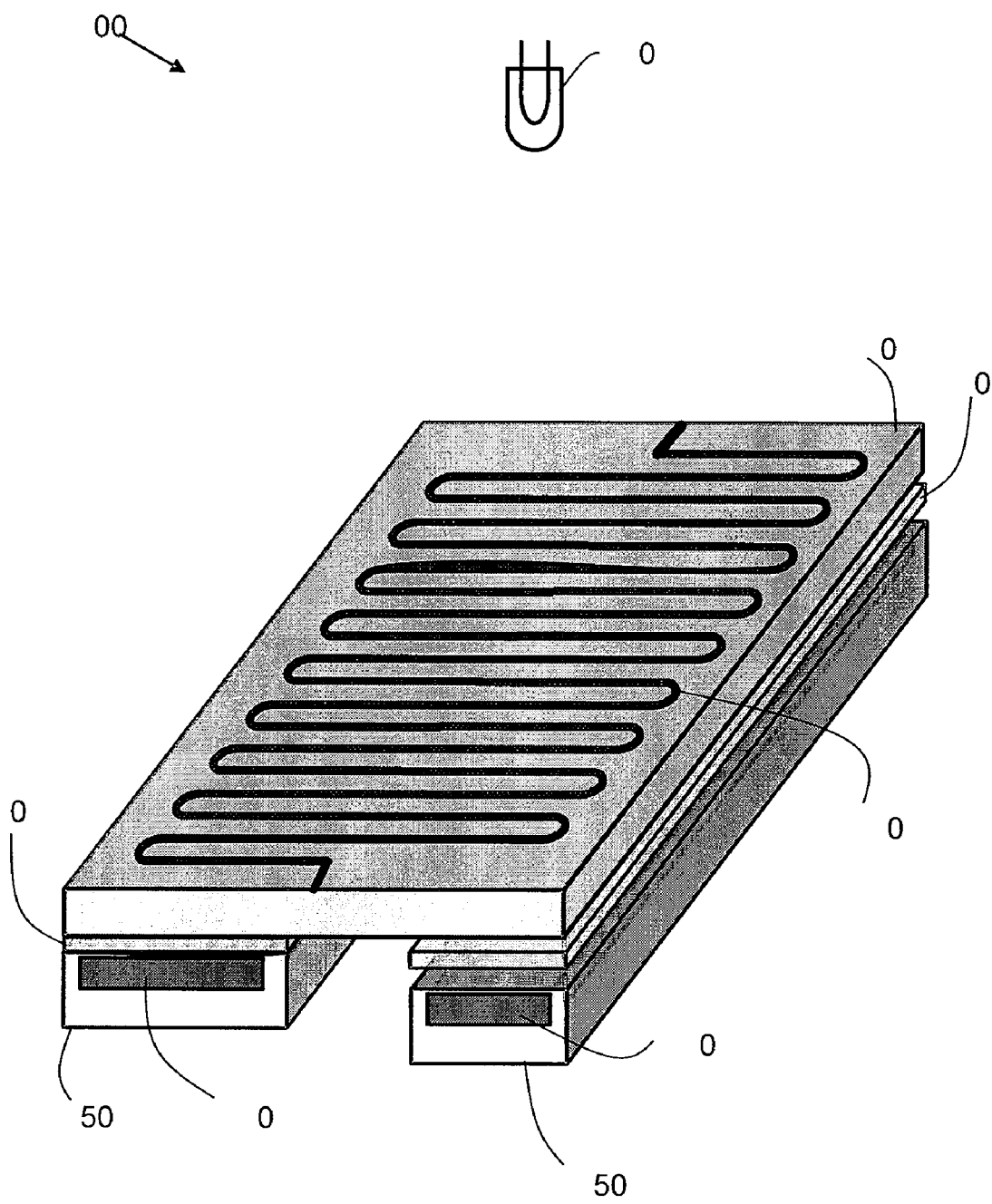
FIG. 7 illustrates an apparatus in accordance with another embodiment.

FIG. 7 illustrates an apparatus 700 in accordance with a third exemplary embodiment. Apparatus 700 includes a microfluidic chip 730 including at least one microfluidic channel 710. In the illustrated embodiment, channel 710 is generally in the shape of a sine wave.

Figure 8:
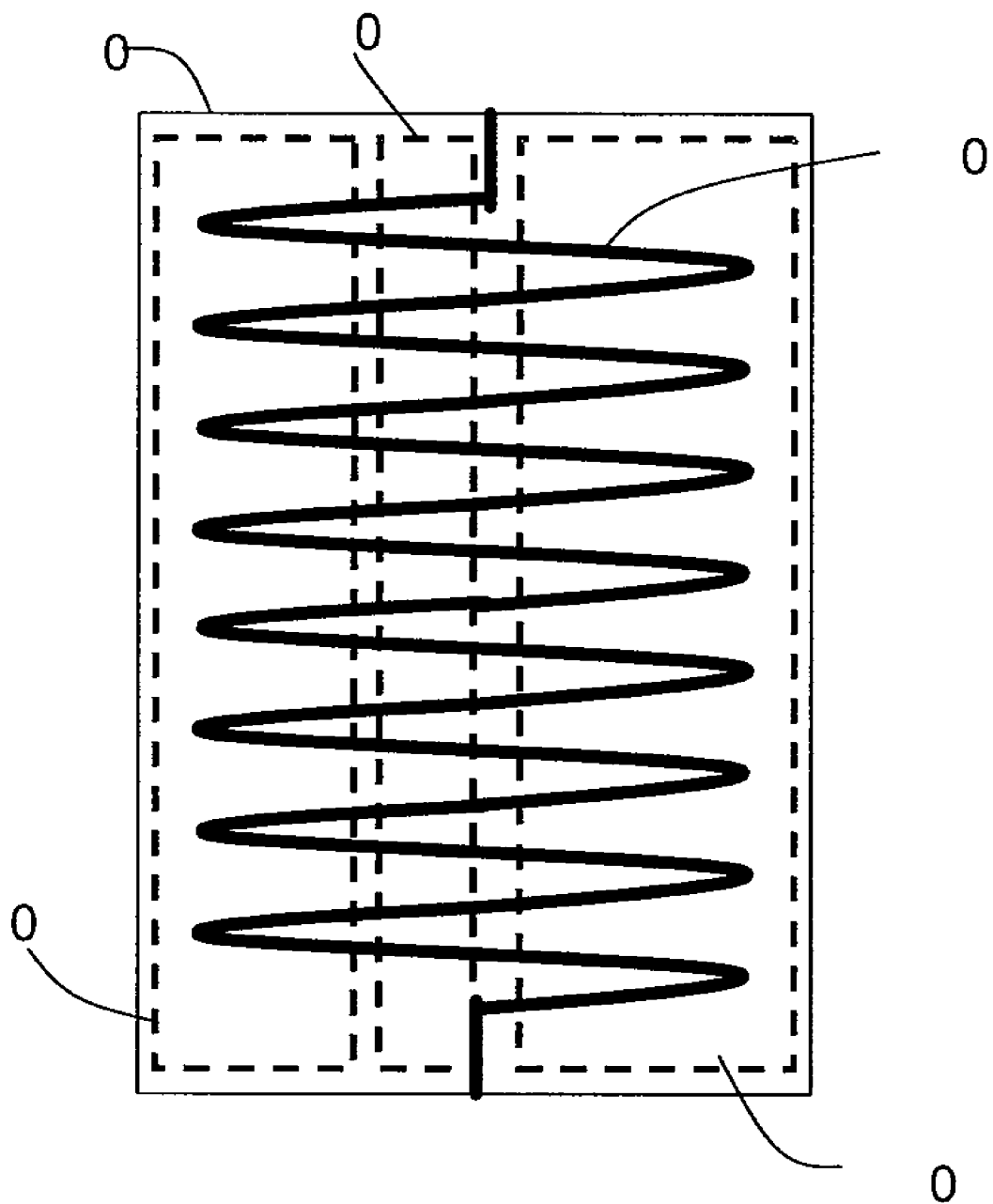
FIG. 8 illustrates a top view of the microfluidic chip illustrated in FIG. 7.

A temperature controller (e.g., radiation source 720 or other heater, heat-exchange channels 750a,b for containing a heat-exchange fluid 760a,b, and absorptive elements 790a,b) is configured and arranged so as to create three distinct temperature zones (zone 830a, zone 830b, and zone 830c—see FIG. 8).

Although a particular arrangement of heating/cooling elements are shown, this is only for illustration, as any kind of heaters and heat sinks may be used to create the three unique temperature zones. Accordingly, this embodiment should not be limited to any particular heating or cooling mechanism.

Preferably, the temperature in each zone is generally held constant and the temperature of any particular zone is preferably different than the temperatures of the other two zones. For example, the temperature of zone 803a may be set to about 72° C., the temperature of zone 803b may be set to about 52° C. and the temperature of zone 803C may be set to about 94° C.

Figure 9:
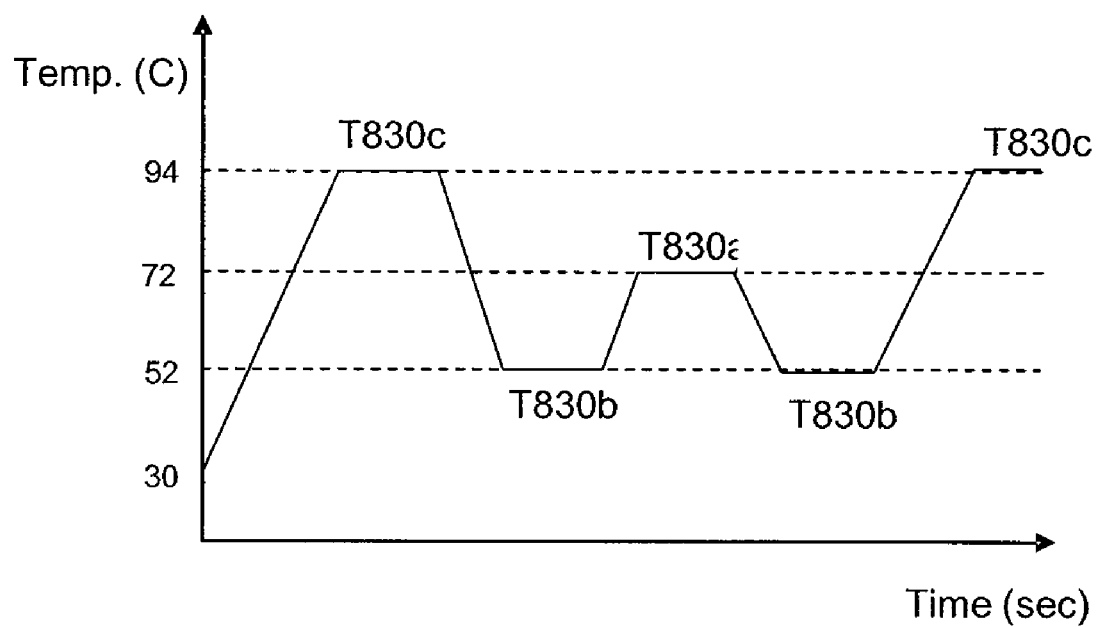
FIG. 9. illustrates an example temperature profile.

As further illustrated in FIG. 8, a first set of segments of channel 710 (i.e., the top section of channel 710) lie within zone 830a, a second set of segments of channel 710 (i.e., the middle section of channel 710) lie within zone 830b, and a third set of segments of channel 710 (i.e., the bottom section of channel 710) lie within zone 830c, such that a sample flowing through channel 701 would be exposed to region 830c, then 830b, then 830a, then 830b, then 830c again where the sequence repeats. This feature is illustrated in FIG. 9, which shows the temperature profile of a sample moving through the microfluidic channel 710.

Apparatus 700 may be used to amplify DNA. For example, a fluidic sample containing PCR reagents may be introduce into channel 710 and forced to move through channel 710. Moving the sample through the microfluidic channel 710 can be accomplished by a variety of methods, for example, via conventional methods of pressure-driven flow and the flow rates can vary, for example between 10 nanoliters per minute to 1 ml per minute.

As the sample traverses channel 710, the sample is exposed to the different temperature regions in a cyclical fashion. Thus, if the temperatures of the temperature zone are set as described above, then DNA amplification may occur. When apparatus 700 is used for DNA amplification, channel 710 may be configured so that the sample will cycle through the temperature regions at least about 10 times, thus providing a sufficient amount of PCR cycles.

While the present invention has been described with reference to exemplary embodiments, it is to be understood that the invention is not limited to the disclosed exemplary embodiments.

What is claimed is:

1. An apparatus for use in carrying out a reaction by thermal cycling, comprising:
   a microfluidic chip;
   a microfluidic channel formed in the microfluidic chip, the microfluidic channel having at least one wall;
   an electromagnetic energy source configured and arranged to output radiation such that the radiation illuminates at least a portion of the microfluidic channel;
   an energy absorption element which is present in or on one or more walls of the microfluidic channel or which is present in a sample within the microfluidic channel;
   wherein,
   the energy absorption element is configured to absorb at least a portion of the radiation, and, thus, heat when illuminated by the radiation, wherein the absorption element is positioned such that when the absorption element is heated by the radiation the absorption element transfers heat to a sample that is in the microfluidic channel; and
   a heat-exchange channel having a generally U-shaped cross section and containing a heat exchange fluid, wherein the heat-exchange channel is located below the microfluidic channel and wherein the heat-exchange channel is configured to allow both introduction and removal of a heat exchange fluid to facilitate thermal cycling in the microfluidic channel.

2. The apparatus of claim 1, wherein the energy absorption element forms a part of the microfluidic channel.

3. The apparatus of claim 1, wherein the energy absorption element is applied to and adheres to a wall of the microfluidic channel.

4. The apparatus of claim 3, wherein the energy absorption element comprises a colored coating.

5. The apparatus of claim 4, wherein the coating is generally dark in color.

6. The apparatus of claim 5, wherein the energy absorption element comprises paint that is generally black in color.

7. The apparatus of claim 1, wherein the energy absorbing element is suspended in the sample.

8. The apparatus of claim 7, wherein the energy absorbing element comprises a plurality of small energy absorbing particles.

9. The apparatus of claim 1, wherein the microfluidic channel runs through the heat-exchange channel.

10. The apparatus of claim 9, wherein a wall of the heat-exchange channel is rough.

11. The apparatus of claim 1, wherein the electromagnetic energy source comprises a laser.

12. The apparatus of claim 1, wherein the laser is configured to output electromagnetic radiation having a wavelength of between about 100 nanometers to 300 micrometers.

13. The apparatus of claim 12, wherein the laser is configured to output electromagnetic radiation having a wavelength of between about 200 nanometers to 20 microns.

14. The apparatus of claim 1, wherein the energy absorption element is positioned below the microfluidic channel.

15. An apparatus for use in carrying out a reaction by thermal cycling, comprising:
    a microfluidic chip comprising a microfluidic channel for containing a reaction sample;
    an energy absorbing element that is applied to and/or forms part of the microfluidic channel and which is configured to absorb radiation;
    heating means to heat the reaction sample;
    cooling means to cool the reaction sample; wherein the cooling means comprises a heat-exchange channel having a generally U-shaped cross section and containing a heat exchange fluid, wherein the heat-exchange channel is located below the microfluidic channel and wherein the heat-exchange channel is configured to allow both introduction and removal of a heat exchange fluid to facilitate thermal cycling in the microfluidic channel;
    sensor means to sense the temperature of the reaction sample; and
    control means coupled to the sensor means for controlling the heating means.

16. The apparatus of claim 15, wherein the heating means comprises an electromagnetic energy source operable to expose the microfluidic channel with radiation produced by the energy source.

17. The apparatus of claim 16, wherein the electromagnetic energy source is an infra-red energy source.

18. The apparatus of claim 16, wherein the electromagnetic energy source comprises a laser.

19. The apparatus of claim 18, wherein the laser is configured to output electromagnetic radiation having a wavelength of between about 100 nanometers and about 300 micrometers.

20. The apparatus of claim 15, wherein the control means is a controller.

21. The apparatus of claim 20, wherein the controller is a PID controller.

22. The apparatus of claim 15, wherein the microfluidic channel runs through the heat-exchange channel.

23. The apparatus of claim 15, wherein the energy absorbing element comprises a dark colored coating, and the dark colored coating is applied to a wall of the microfluidic channel.

24. A method for rapid thermal cycling, comprising:
    (a) obtaining a microfluidic chip described in claim 1 having a microfluidic channel for receiving a solution comprising real-time PCR reagents;
    (b) introducing a solution comprising real-time PCR reagents into the microfluidic channel;
    (c) heating the solution while the solution moves through the microfluidic channel, wherein the act of heating the solution comprises exposing the microfluidic channel to electromagnetic radiation;
    (d) after heating the solution, cooling the solution while the solution moves through the channel; and
    (e) repeating steps (c) and (d) a number of times, wherein an energy absorbing element configured to absorb the electromagnetic radiation is suspended within the solution and/or forms part of the chip.

25. The method of claim 24, wherein prior to the step of introducing a solution comprising real-time PCR reagents into the microfluidic channel, the method comprises: obtaining the solution, obtaining an energy absorbing element, and adding the element to the solution.

26. The method of claim 25, wherein the energy absorbing element comprises a plurality of energy absorbing particles.

27. The method of claim 24, wherein the energy absorbing element forms part of the microfluidic chip.

28. The method of claim 27, wherein the energy absorbing element is applied to and adheres to a wall of the microfluidic channel.

29. The method of claim 28, wherein the energy absorption element comprises a colored coating.

30. The method of claim 29, wherein the coating is generally dark in color.

31. The method of claim 30, wherein the energy absorption element comprises paint that is generally black in color.

32. The method of claim 24, wherein the microfluidic chip also has a heat-exchange channel.

33. The method of claim 32, wherein the heat-exchange channel is generally V-shaped and the microfluidic channel runs through the heat-exchange channel.

34. The method of claim 33, wherein the act of heating the sample further comprises introducing into the heat-exchange channel an insulating fluid for insulating the microfluidic channel.

35. The method of claim 34, wherein the act of cooling the sample comprises introducing into the heat-exchange channel a cooling fluid for cooling the solution.

36. An apparatus for performing DNA amplification, comprising:
    a microfluidic chip having at least one microfluidic channel that is generally in the shape of a sine wave; and
    a temperature controller comprising a heat source and a heat-exchange channel having a generally U-shaped cross section and containing a heat exchange fluid, wherein the heat-exchange channel is located below the microfluidic channel, wherein the heat-exchange channel is configured to allow both introduction and removal of a heat exchange fluid to facilitate thermal cycling in the microfluidic channel wherein
    the temperature controller is configured and arranged so as to create three distinct and generally constant temperature zones: a first temperature zone, a second temperature zone that does not overlap with the first zone, and a third temperature zone that does not overlap with either the first or second temperature zone,
    wherein
    a top section of the channel is located within the first temperature zone,
    a middle section of the channel is located within the second temperature zone, and
    a bottom section of the channel is located within the third temperature zone.

* * * * *